: US 9,474,334 B2
: Oct. 25, 2016

United States Patent
Jonsson et al.

(54) FASTENER MEMBER FOR AFFIXATION TO A STRUCTURE IN AN ORTHOPEDIC DEVICE AND METHOD FOR SECURING THE SAME

(71) Applicant: OSSUR HF, Reykjavik (IS)

(72) Inventors: Helgi Jonsson, Reykjavik (IS); Arni Thor Ingimundarson, Gardabaer (IS); Bjorn Omarsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 96 days.

(21) Appl. No.: 14/077,436

(22) Filed: Nov. 12, 2013

(65) Prior Publication Data

US 2014/0130333 A1    May 15, 2014

Related U.S. Application Data

(60) Provisional application No. 61/725,539, filed on Nov. 13, 2012.

(51) Int. Cl.
    *A44B 13/00*      (2006.01)
    *A41D 13/05*      (2006.01)
    *A61F 5/01*      (2006.01)

(52) U.S. Cl.
    CPC ....... *A44B 13/0035* (2013.01); *A41D 13/0562* (2013.01); *A44B 13/00* (2013.01); *A61F 5/01* (2013.01); *A61F 2005/0172* (2013.01); *Y10T 24/3484* (2015.01); *Y10T 29/49947* (2015.01)

(58) Field of Classification Search
    CPC .. A61F 5/0123; A61F 5/0125; A61F 5/0109; A61F 13/062; F16B 5/07; A44B 18/0069
    See application file for complete search history.

(56) References Cited

U.S. PATENT DOCUMENTS

| | | | |
|---|---|---|---|
| 157,883 | A | 12/1874 | Spruce |
| 665,985 | A | 1/1901 | White |
| 667,768 | A | 2/1901 | Poy |
| 676,810 | A | 6/1901 | Young |
| 718,018 | A | 1/1903 | Northrop |
| 777,585 | A | 12/1904 | Beatty |
| 782,460 | A | 2/1905 | Northrop |
| 810,537 | A | 1/1906 | Hopkins |

(Continued)

FOREIGN PATENT DOCUMENTS

| | | |
|---|---|---|
| CH | 61400 A | 9/1913 |
| DE | 846895 C | 8/1952 |

(Continued)

OTHER PUBLICATIONS

International Search Report and Written Opinion from PCT Application No. PCT/IB2010/003540, Oct. 13, 2011.

(Continued)

*Primary Examiner* — Michael P Ferguson
(74) *Attorney, Agent, or Firm* — Workman Nydegger

(57) ABSTRACT

A fastener member for mechanical affixation to a structure includes a base having first and second sides, a plurality of fastening elements integrally formed and extending from a first side of the base, and at least one affixation element extending from the second side of the base and arranged to mechanically affix to an attachment opening of a structure. A system includes a structure and a fastener member for mechanical affixation to the structure. A method includes affixing the fastener member to a structure.

18 Claims, 6 Drawing Sheets

(56) References Cited

U.S. PATENT DOCUMENTS

| | | | |
|---|---|---|---|
| 937,478 A | 10/1909 | Sims | |
| 944,673 A | 12/1909 | Harrison | |
| 1,148,444 A | 7/1915 | Crawford | |
| 1,153,334 A | 9/1915 | Oswald | |
| 1,227,700 A | 5/1917 | Tucker | |
| 1,328,541 A | 1/1920 | Palmer | |
| 1,510,408 A | 9/1924 | Lychou | |
| 1,622,211 A | 3/1927 | Sheehan | |
| 2,032,923 A | 3/1936 | Eldridge | |
| 2,179,903 A | 11/1939 | Spears | |
| 2,467,907 A | 4/1949 | Peckham | |
| 2,573,866 A | 11/1951 | Murphy et al. | |
| 2,717,841 A | 9/1955 | Biefeld et al. | |
| 2,935,065 A | 5/1960 | Homier et al. | |
| 3,031,730 A * | 5/1962 | Morin | 24/444 |
| 3,046,981 A | 7/1962 | Biggs, Jr. et al. | |
| 3,089,486 A | 5/1963 | Pike | |
| 3,266,113 A | 8/1966 | Flanagan, Jr. | |
| 3,463,147 A | 8/1969 | Stubbs | |
| 3,514,313 A | 5/1970 | Martel et al. | |
| 3,520,765 A | 7/1970 | Bateman | |
| 3,528,412 A | 9/1970 | McDavid | |
| 3,561,436 A | 2/1971 | Gaylord, Jr. | |
| 3,581,741 A | 6/1971 | Rosman et al. | |
| 3,594,863 A | 7/1971 | Erb | |
| 3,594,865 A | 7/1971 | Erb | |
| 3,742,557 A | 7/1973 | Francois | |
| 3,743,147 A | 7/1973 | Wilczynski | |
| 3,752,619 A | 8/1973 | Menzin et al. | |
| 3,758,657 A | 9/1973 | Menzin et al. | |
| 3,789,842 A | 2/1974 | Froimson | |
| 3,808,648 A | 5/1974 | Billarant et al. | |
| 3,851,357 A * | 12/1974 | Ribich et al. | 24/306 |
| 3,877,426 A | 4/1975 | Nirschl | |
| 3,916,077 A | 10/1975 | Damrau | |
| 3,927,881 A | 12/1975 | Lemelson et al. | |
| 3,945,046 A | 3/1976 | Stromgren | |
| 3,955,565 A | 5/1976 | Johnson, Jr. | |
| 4,193,395 A | 3/1980 | Gruber | |
| 4,204,532 A | 5/1980 | Lind et al. | |
| 4,240,414 A | 12/1980 | Theisler | |
| 4,269,179 A | 5/1981 | Burton et al. | |
| 4,269,181 A | 5/1981 | Delannoy | |
| 4,275,716 A | 6/1981 | Scott, Jr. | |
| 4,280,489 A | 7/1981 | Johnson, Jr. | |
| 4,291,072 A | 9/1981 | Barrett et al. | |
| 4,296,744 A | 10/1981 | Palumbo | |
| 4,304,560 A | 12/1981 | Greenwood | |
| 4,336,279 A | 6/1982 | Metzger | |
| 4,372,298 A | 2/1983 | Lerman | |
| 4,381,768 A | 5/1983 | Erichsen et al. | |
| 4,386,723 A | 6/1983 | Mule | |
| 4,396,012 A | 8/1983 | Cobiski | |
| 4,470,857 A | 9/1984 | Casalou | |
| 4,472,461 A | 9/1984 | Johnson | |
| 4,506,661 A | 3/1985 | Foster | |
| 4,528,440 A | 7/1985 | Ishihara | |
| 4,554,913 A | 11/1985 | Womack et al. | |
| 4,572,170 A | 2/1986 | Cronk et al. | |
| 4,617,214 A | 10/1986 | Billarant | |
| 4,632,098 A | 12/1986 | Grundei et al. | |
| 4,677,713 A | 7/1987 | Copp | |
| 4,693,921 A | 9/1987 | Billarant et al. | |
| D292,529 S | 10/1987 | Saare | |
| 4,768,500 A | 9/1988 | Mason et al. | |
| 4,775,310 A | 10/1988 | Fischer | |
| D298,568 S | 11/1988 | Womack et al. | |
| 4,782,605 A | 11/1988 | Chapnick | |
| 4,791,916 A | 12/1988 | Paez | |
| 4,794,028 A | 12/1988 | Fischer | |
| 4,801,138 A | 1/1989 | Airy et al. | |
| 4,802,939 A | 2/1989 | Billarant et al. | |
| 4,805,606 A | 2/1989 | McDavid, III | |
| 4,854,308 A | 8/1989 | Drillio | |
| 4,856,501 A | 8/1989 | Castillo et al. | |
| 4,856,502 A | 8/1989 | Ersfeld et al. | |
| 4,872,243 A | 10/1989 | Fischer | |
| 4,922,929 A | 5/1990 | DeJournett | |
| 4,933,035 A | 6/1990 | Billarant et al. | |
| 4,953,543 A | 9/1990 | Grim et al. | |
| 4,961,544 A | 10/1990 | Bidoia | |
| 4,966,133 A | 10/1990 | Kausek | |
| 4,989,593 A | 2/1991 | Campagna et al. | |
| 4,991,574 A | 2/1991 | Pocknell | |
| 4,991,640 A | 2/1991 | Verkindt et al. | |
| 5,016,621 A | 5/1991 | Bender | |
| 5,018,514 A | 5/1991 | Grood et al. | |
| 5,020,196 A * | 6/1991 | Panach et al. | 24/590.1 |
| 5,022,109 A | 6/1991 | Pekar | |
| 5,063,916 A | 11/1991 | France et al. | |
| 5,067,772 A | 11/1991 | Koa | |
| 5,077,870 A | 1/1992 | Melbye et al. | |
| 5,085,210 A | 2/1992 | Smith, III | |
| 5,112,296 A | 5/1992 | Beard et al. | |
| 5,154,682 A | 10/1992 | Kellerman | |
| 5,157,813 A | 10/1992 | Carroll | |
| 5,181,331 A | 1/1993 | Berger | |
| 5,242,379 A | 9/1993 | Harris et al. | |
| 5,267,951 A | 12/1993 | Ishii | |
| 5,277,697 A | 1/1994 | France et al. | |
| 5,277,698 A | 1/1994 | Taylor | |
| 5,288,287 A | 2/1994 | Castillo et al. | |
| 5,302,169 A | 4/1994 | Taylor | |
| 5,314,455 A | 5/1994 | Johnson, Jr. et al. | |
| 5,316,547 A | 5/1994 | Gildersleeve | |
| 5,322,729 A | 6/1994 | Heeter et al. | |
| 5,334,135 A | 8/1994 | Grim et al. | |
| 5,344,135 A | 9/1994 | Isobe et al. | |
| 5,368,549 A | 11/1994 | McVicker | |
| 5,383,845 A | 1/1995 | Nebolon | |
| 5,397,296 A | 3/1995 | Sydor et al. | |
| 5,415,625 A | 5/1995 | Cassford et al. | |
| 5,431,623 A | 7/1995 | Rice | |
| 5,437,619 A | 8/1995 | Malewicz et al. | |
| 5,445,602 A | 8/1995 | Grim et al. | |
| 5,449,341 A | 9/1995 | Harris | |
| 5,458,565 A | 10/1995 | Tillinghast, III et al. | |
| 5,468,219 A | 11/1995 | Crippen | |
| 5,472,413 A | 12/1995 | Detty | |
| 5,474,524 A | 12/1995 | Carey | |
| 5,497,513 A | 3/1996 | Arabeyre et al. | |
| 5,500,268 A | 3/1996 | Billarant | |
| 5,512,039 A | 4/1996 | White | |
| 5,513,658 A | 5/1996 | Goseki | |
| 5,514,081 A | 5/1996 | Mann | |
| 5,527,269 A | 6/1996 | Reithofer | |
| 5,540,982 A | 7/1996 | Scholz et al. | |
| 5,542,911 A | 8/1996 | Cassford et al. | |
| 5,562,605 A | 10/1996 | Taylor | |
| 5,599,288 A | 2/1997 | Shirley et al. | |
| 5,614,045 A | 3/1997 | Billarant | |
| 5,635,201 A | 6/1997 | Fabo | |
| 5,638,588 A | 6/1997 | Jungkind | |
| 5,654,070 A | 8/1997 | Billarant | |
| 5,656,226 A | 8/1997 | McVicker | |
| 5,665,449 A | 9/1997 | Billarant | |
| 5,695,452 A | 12/1997 | Grim et al. | |
| 5,713,837 A | 2/1998 | Grim et al. | |
| D392,877 S * | 3/1998 | Eguchi | D8/382 |
| 5,737,854 A | 4/1998 | Sussmann | |
| 5,759,167 A | 6/1998 | Shields, Jr. et al. | |
| 5,769,808 A | 6/1998 | Matthijs et al. | |
| 5,774,902 A | 7/1998 | Gehse | |
| 5,795,640 A | 8/1998 | Billarant | |
| 5,823,981 A | 10/1998 | Grim et al. | |
| 5,840,398 A | 11/1998 | Billarant | |
| 5,857,988 A | 1/1999 | Shirley | |
| 5,857,989 A | 1/1999 | Smith, III | |
| 5,865,776 A | 2/1999 | Springs | |
| 5,865,777 A | 2/1999 | Detty | |
| 5,865,782 A | 2/1999 | Fareed | |
| 5,873,848 A | 2/1999 | Fulkerson | |
| 5,891,061 A | 4/1999 | Kaiser | |
| 5,900,303 A | 5/1999 | Billarant | |

(56) References Cited

U.S. PATENT DOCUMENTS

| | | |
|---|---|---|
| 5,916,187 A | 6/1999 | Brill |
| 5,948,707 A | 9/1999 | Crawley et al. |
| 5,971,946 A | 10/1999 | Quinn et al. |
| 6,010,474 A | 1/2000 | Wycoki |
| 6,021,780 A | 2/2000 | Darby |
| 6,022,617 A | 2/2000 | Calkins |
| 6,024,712 A | 2/2000 | Iglesias et al. |
| 6,063,048 A | 5/2000 | Bodenschatz et al. |
| 6,110,138 A | 8/2000 | Shirley |
| 6,111,138 A | 8/2000 | Van Wijck et al. |
| 6,142,965 A | 11/2000 | Mathewson |
| 6,152,893 A | 11/2000 | Pigg et al. |
| 6,159,583 A | 12/2000 | Calkins |
| 6,163,939 A | 12/2000 | Lacey et al. |
| 6,187,247 B1 | 2/2001 | Buzzell et al. |
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,402,713 B1 | 6/2002 | Doyle |
| 6,405,731 B1 | 6/2002 | Chiang |
| 6,413,232 B1 | 7/2002 | Townsend et al. |
| 6,416,074 B1 | 7/2002 | Maravetz et al. |
| 6,451,239 B1 | 9/2002 | Wilson |
| 6,461,318 B2 | 10/2002 | Freeman et al. |
| 6,485,776 B2 | 11/2002 | Janusson et al. |
| 6,520,926 B2 | 2/2003 | Hall |
| 6,540,703 B1 | 4/2003 | Lerman |
| 6,540,709 B1 | 4/2003 | Smits |
| 6,543,158 B2 | 4/2003 | Dieckhaus |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 * | 5/2004 | Iverson et al. ............... 16/4 |
| 6,769,155 B2 | 8/2004 | Hess et al. |
| 6,773,411 B1 | 8/2004 | Alvarez |
| 6,861,371 B2 | 3/2005 | Blaszcykiewicz |
| 6,861,379 B1 | 3/2005 | Blaszcykiewicz |
| 6,898,804 B2 | 5/2005 | Sandler |
| 6,898,826 B2 | 5/2005 | Draper et al. |
| 6,936,020 B2 | 8/2005 | Davis |
| D519,637 S | 4/2006 | Nordt, III et al. |
| D519,638 S | 4/2006 | Nordt, III et al. |
| 7,025,738 B2 | 4/2006 | Hall |
| D520,141 S | 5/2006 | Nordt, III et al. |
| D521,644 S | 5/2006 | Nordt, III et al. |
| 7,037,287 B2 | 5/2006 | Cormier et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,303,539 B2 | 12/2007 | Binder et al. |
| 7,367,958 B2 | 5/2008 | McBean et al. |
| 7,448,115 B2 * | 11/2008 | Howell et al. ............... 24/3.12 |
| 7,716,792 B2 | 5/2010 | Clarner |
| 7,762,973 B2 | 7/2010 | Einarsson et al. |
| 7,874,996 B2 | 1/2011 | Weinstein et al. |
| 7,937,973 B2 | 5/2011 | Sorensen et al. |
| 8,281,463 B2 | 10/2012 | Hammer |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0125605 A1 | 9/2002 | Lacey et al. |
| 2002/0132086 A1 | 9/2002 | Su-Tuan |
| 2003/0032907 A1 | 2/2003 | Prahl |
| 2003/0069531 A1 | 4/2003 | Hall |
| 2003/0204156 A1 | 10/2003 | Nelson et al. |
| 2004/0002674 A1 | 1/2004 | Sterling |
| 2004/0054311 A1 | 3/2004 | Sterling |
| 2004/0058102 A1 | 3/2004 | Baychar |
| 2004/0137178 A1 | 7/2004 | Janusson et al. |
| 2004/0137192 A1 * | 7/2004 | McVicker ............... 428/100 |
| 2004/0153016 A1 | 8/2004 | Salmon et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0020951 A1 | 1/2005 | Gaylord et al. |
| 2005/0038367 A1 | 2/2005 | McCormick et al. |
| 2005/0081339 A1 | 4/2005 | Sakabayashi |
| 2005/0159691 A1 | 7/2005 | Turrini et al. |
| 2005/0160627 A1 | 7/2005 | Dalgaard et al. |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verade et al. |
| 2006/0090806 A1 | 5/2006 | Friedline et al. |
| 2006/0116619 A1 | 6/2006 | Weinstein et al. |
| 2006/0135902 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0191110 A1 | 8/2006 | Howell et al. |
| 2007/0083136 A1 | 4/2007 | Einarsson |
| 2007/0167892 A1 | 7/2007 | Gramza et al. |
| 2007/0185425 A1 | 8/2007 | Einarsson et al. |
| 2007/0225824 A1 | 9/2007 | Einarsson |
| 2008/0034459 A1 | 2/2008 | Nordt, III et al. |
| 2008/0229556 A1 * | 9/2008 | Hammer ............... 24/444 |
| 2009/0099562 A1 | 4/2009 | Ingimudarson et al. |
| 2009/0126413 A1 | 5/2009 | Sorensen et al. |
| 2010/0068464 A1 * | 3/2010 | Meyer ............... 428/161 |
| 2010/0125231 A1 | 5/2010 | Knecht |
| 2011/0057466 A1 * | 3/2011 | Sachee et al. ............... 296/37.3 |
| 2011/0275970 A1 | 11/2011 | Paulos et al. |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2014/0121579 A1 | 5/2014 | Hinds |

FOREIGN PATENT DOCUMENTS

| | | | |
|---|---|---|---|
| DE | 100 04 561 A1 | 8/2001 | |
| DE | 20 2004 012892 U1 | 11/2004 | |
| EP | 0050769 A1 | 5/1982 | |
| EP | 0 196 204 A2 | 10/1986 | |
| EP | 0 464 754 A1 | 1/1992 | |
| EP | 0 465 983 A1 | 1/1992 | |
| EP | 0611069 B1 | 8/1994 | |
| EP | 2612626 A2 | 7/2013 | |
| FR | 2399811 A1 | 3/1979 | |
| FR | 2553996 A1 | 5/1985 | |
| FR | 2766359 A1 | 1/1999 | |
| GB | 1 209 413 | * 10/1970 | ............... F16B 5/12 |
| GB | 2136294 A | 9/1984 | |
| GB | 2 455 972 A | 7/2009 | |
| WO | 88/01855 A1 | 3/1988 | |
| WO | 94/00082 A1 | 1/1994 | |
| WO | 00/49982 A1 | 8/2000 | |
| WO | 00/70984 A1 | 11/2000 | |
| WO | 2006/015599 A1 | 2/2006 | |
| WO | 2006/069221 A2 | 6/2006 | |

(56) References Cited

FOREIGN PATENT DOCUMENTS

| WO | 2006/069222 A2 | 6/2006 |
|---|---|---|
| WO | 2008/115376 A1 | 9/2008 |
| WO | 2010/117749 A2 | 10/2010 |
| WO | 2011/073803 A2 | 6/2011 |

OTHER PUBLICATIONS

International Search Report and Written Opinion from PCT Application No. PCT/US2008/03237, Jul. 14, 2008.
Advertisement: "Custom Engineered Fabrics and Products for Advanced High Performance", 1 page, Gehring Textiles retrieved from the Internet on Dec. 15, 2000; http://www.gehringtextiles.com/d3.html.
Article: "Thermoplastic Elastomers TPE, TPR, TPV," 6 pages, retrieved from the Internet on Mar. 14, 2007; http://www.bpf.com/uk/bpfindustry/plastics_materials_thermplasrubber_TBR.cfm.
Advertisement: "Axiom", 3 pages, Bledsoe Medical Technology, Inc., retrieved from the Internet Jun. 15, 2005; http://www.bledsoebrace.com/custom/axiom.asp.
Advertisement: "Bellacure: the Treatement Device", 6 pages, Bellacure, Inc., retrieved from the Internet on Jan. 5, 2006, http://www.bellacure.com/products/index.htm.
Advertisement: "Lerman 3-Point Knee Orthosis", 2 pages, Becker Orthopedic of Troy, MI, retrieved from the Internet on Feb. 23, 2006, http://www.beckerortho.com/knee/3-point.html.
Advertisement: "M2 Inc. Parts Catalog", 3 pages, M2 Inc of Winooski, VT, retrieved from the Internet on Mar. 29, 2005, http://www.m2intl.com/medical.MedCisr.htm.
Advertisement: "McDavid Knee Guard and 155 Ligament Augmentation System", 3 pages, Advanced Brace of Irving, TX, retrieved from the Internet on Mar. 8, 2005, http://www.supports4u.com/mcdavid/kneeguard.htm.
Advertisement: "Triax", 1 page, LANXESS AG, retrieved from the Internet on Mar. 8, 2005, http://www.techcenter.lanxess.com/sty/emea/en/products/description/57/index.jsp?print=true&pid=57.
Advertising Brochure: "Anderson Knee Stabler", 4 pages, Omni Scientific, Inc. of Lafayette, CA (2005).
Advertising Brochure: "Fusion", 6 pages, Breg, Inc. of Vista, CA (2005).
Advertising Brochure: "Fusion XT", 2 pages, Breg, Inc. of Vista, CA (2005).
Advertising Brochure: "GII Unloader Select", 2 pages, Ossur HF of Reykjavik, Iceland, retrieved from the Internet on Mar. 8, 2005, http://www.ossur.com/print.asp?PageID-1729.
Advertising Brochure: "Lerman Multi-Ligaments Knee Control Orthosis", 2 pages, Zinco Industries, Inc. of Montrose, CA (1985).
Advertising Brochure: "NuKO Camp", 6 pages, Camp International, Inc., Jackson, MI (1984).
Advertising Brochure: "OTI Brace", 4 pages, Orthopedic Technology, Inc., of San Leandro, CA (2005).
Advertising Brochrue: "The Four Axioms of Functional Bracing", 1 page, Bledsoe by Medical Technology, Inc. (2005).
Advertising Brochure: "The Leader in Knee Motion Management", 8 pages, Donjoy, Carlsbad, CA (2005).
Advertising Brochure: "The Lenox Hill Lightweight", 1 page, Lenox Hill Brace, Inc., New York, NY (2005).
Advertising Brochure: "XCL System", 2 pages, Innovation Sports of Foothill Ranch, CA (2005).
Cousins, s., et al., "An Orthosis for Medial or Lateral Stabilization of Arthritic Knees", Orthotics and Prosthetics, vol. 29, No. 4, pp. 21-26, Dec. 1975.
"Osteoarthritis of the Knee: An Information Booklet", 12 pages, Arthritis Research Campaign, retrieved from the internet on Dec. 14, 2004, http://www.arc.org/uk/about_arth/booklets/6027/6027.htm.
Reference: "Anatomical Planes", 1 page, retrieved from the Internet on Mar. 26, 20055, http://www.spineuniverse.com/displayarticle/phpo/article10233html.
Technical Manual: "Bellacure: Restore your Lifestyle", 10 pages, Bellacure, Inc. (2005).
Technical Manual: "BOA Technology", 3 pages, BOA Technology, Inc. of Steamboat Springs, CO (2005).
"Information on Flexible Polyurethane Foam", IN TOUCH, vol. 4, No. 3, Jul. 1994, 5 pages.
Advertising Brochure: "Freedom to Perform-Fusion", 5 pages, (2005).
Advertising Brochure: "The 9 Innovations of the Axiom Custom Brace", 1 page, Bledose, Medical Technology, Inc. (2005).
International Search Report and Written Opinion of the International Searching Authority from International Application No. PCT/US2014/010410, mailed May 2, 2014.
International Search Report and Written Opinion from International Application No. PCT/US2013/069558, Jul. 3, 2014.
International Search Report and Written Opinion from International Application No. PCT/US2014/010407, Jul. 10, 2014.
International Search Report and Written Opinion from International Application No. PCT/US2014/033266, Jul. 23, 2014.
Extended European Search Report from EP Application No. 10 17 2396, Oct. 8, 2010, 5 pages.
Extended European Search Report from EP Application No. 08 74 2047, Jun. 6, 2013, 6 pages.
International Search Report and Written Opinion from International PCT Application No. PCT/US2014/014192, May 20, 2014.
International Search Report from PCT Application No. PCT/US2016/012346, May 6, 2016.

* cited by examiner

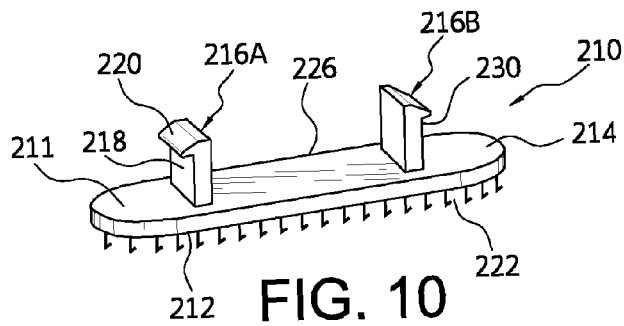
FIG. 10
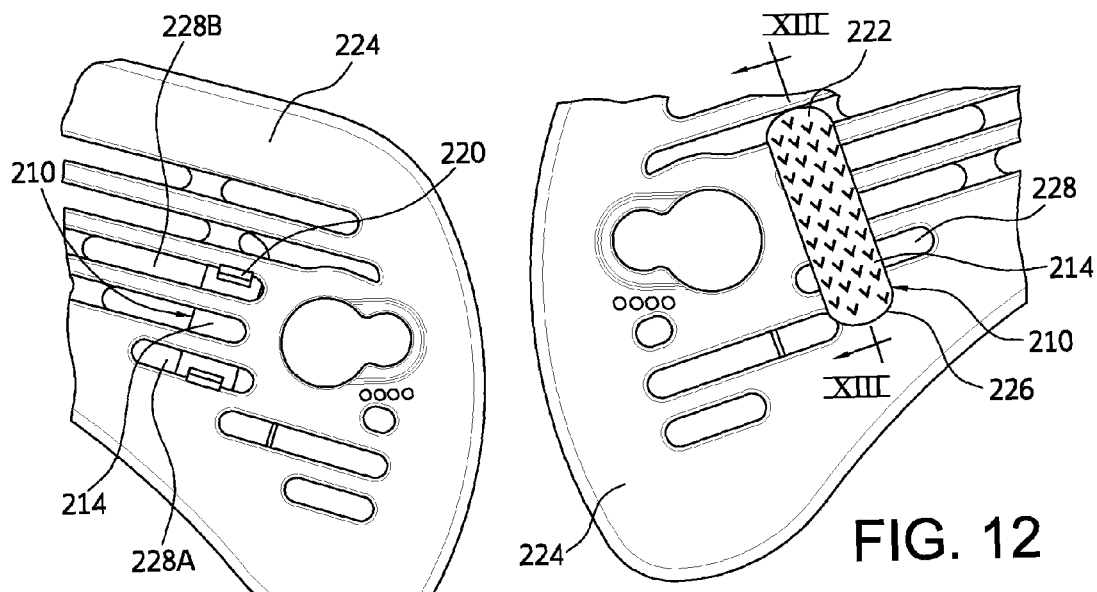
FIG. 11
FIG. 12
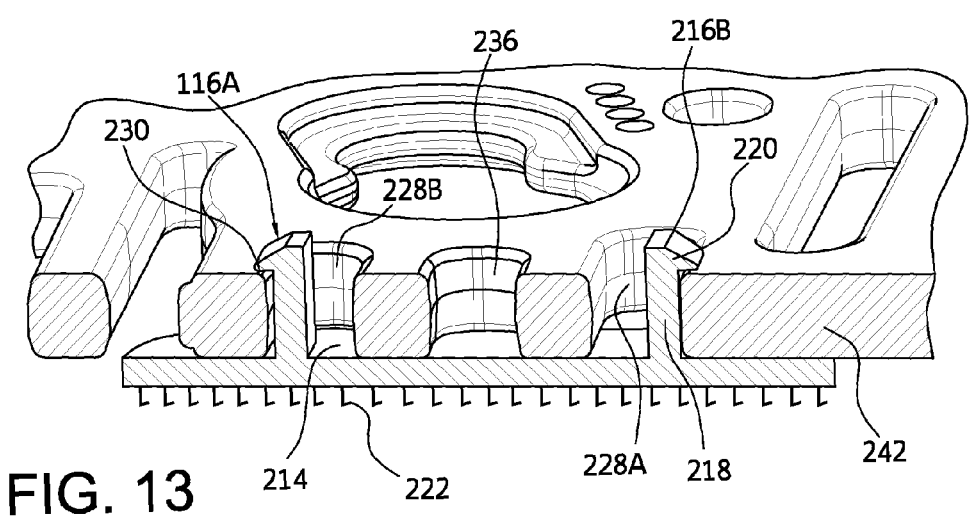
FIG. 13

FASTENER MEMBER FOR AFFIXATION TO A STRUCTURE IN AN ORTHOPEDIC DEVICE AND METHOD FOR SECURING THE SAME

TECHNICAL FIELD

The present disclosure relates to a fastener member for mechanical affixation to a structure, and more particularly to a fastener member including a plurality of fastener elements extending from a side and affixation means for selectively and removably engaging a structure, such as a molded article or frame element in an orthopedic device.

BACKGROUND

In orthopedic devices, textile and/or foam liners are typically attached to frame elements of the device by using hook and loop fastener systems. The liners are provided in part to protect the user from the frame elements which may be rigid or semi-rigid, whereas the liners provide a comfortable interface between the user and the frame element.

It is common practice to use adhesives, ultrasonic welding, or other means to attach pieces of hook material to the frame element, and the liner includes or incorporates hook engageable material or pieces (i.e., loop material) to attach to the hook material pieces on the frame element. It is often found, however, that the shear forces applied to the adhesives on the hook material pieces, coupled with the temperature fluctuations and humidity inherent with orthopedic devices, causes the hook material pieces to slide and migrate over a period of use. This causes problems for the user, as the liner now improperly covers the frame elements, and pressure points may emerge at the edges of the frame element.

The hook material pieces may likewise be used for engaging a strap loop which retains the orthopedic device on the anatomy of the user. Again, adhesive applied hook material pieces tend to migrate which displaces the location of the strap and may lead to a deterioration of the efficacy in securing the device on the user.

In the past, injection molded hook integrally molded onto the frame element has been used to prevent the hook elements sliding and coming lose from the frame element. This is done in such a manner that an insert for the hook elements is placed into an injection molding tool for the frame element and an integrally-formed field of hooks is created during molding or manufacturing of the frame element so the hook is molded directly into the plastic of the frame element. Obviously, this method eliminates the need for adhesively applying the aforementioned hook material pieces and reduces the step of later applying hook material pieces later in the fabrication of an orthopedic device.

While injection molding the hook elements directly onto frame element is effective, it suffers from the drawback that many orthopedic devices do not lend themselves to including integrally molded hook elements. Knee brace shells are commonly post formed onto a user's leg mold after the frame elements are formed by injection molding rendered in a flat configuration. Because the frame elements may be subsequently contoured after the frame element itself is formed, integrally molded hook elements may become damaged during the post-forming and customization process. Due to the inherent differences in shape of each user, the integrally molded hook elements may be at a less favorable location after the frame element has been formed. Known methods for integrally molding hook elements lack flexibility for later modification in location and limit the degree by which frame elements may be customized for an individual user.

SUMMARY

Embodiments according to the disclosure are directed to a fastener member and method for using the same for mechanical affixation to a molded article or frame element, and particularly to a fastener member including a plurality of fastener elements extending from a side and means for selectively and removably engaging a molded article or frame element.

The fastener member embodiments are arranged to mechanically and selectively engage a frame element at post-formation of the frame element. By mechanical engagement, the arrangement of the fastener element obviates the need to adhesively secure hook material pieces to the frame element or integrally form hook elements at the formation of the frame element. By selective engagement, a clinician can place the fastener at many locations suitable for a desired application, such as securing to a liner or engaging a strap. From the arrangement of the fastener element, migration of the hook element is eliminated and damage of hook elements during post-forming of the frame elements is prevented.

The fastener member is arranged for having an affixation element that is releasably affixed to a structure, such that the affixation element can be quickly fixed to the structure without machining, molding or applying adhesive, and can be easily detached from the structure without being damaged.

The fastener member embodiments may retrofit on existing orthopedic devices having frame elements defining suitable openings capable of interengaging various means for affixing the fastener members to the frame element to connect brace components, such as liners, padding, and straps, to the frame element.

A fastener member for mechanical affixation to a structure includes a base having first and second sides, a plurality of fastening elements integrally formed and extending from a first side of the base, and at least one affixation element extending from the second side of the base and arranged to mechanically affix to an attachment opening of a structure.

The at least one affixation element includes a stem protruding from the base and a head extending from the stem. The head may have a length greater than a width of the stem. A plurality of fastening elements may include first and second rows of hook elements, and the hooks of each of the first and second rows extend in opposing directions, respectively.

According to a variation, the base may have a substantially flat back side. The base may be flexible and arranged to accommodate a shape of the structure upon which the fastener member is affixed.

The at least one affixation element may define first and second resiliently flexible side legs spaced apart by gaps on opposed sides of a center leg. A head may form flange segments extending from both of the side legs and have a mirror image of one another. A periphery of the base may be elongate and have rounded edges.

The at least one affixation element may include first and second affixation elements protruding from the base. Each of the first and second affixation elements may define a resiliently flexible side leg carrying a head having a sloped face and extending to a flange. The sloped faces may be arranged in opposed directions relative to the length of the base.

A system has a frame element and a fastener member for mechanical affixation to the frame element. The fastener member is arranged to mechanically affix to an attachment opening of the frame element. The frame element may include an opening through which the at least one affixation element extends. The at least one affixation element has a head defining a dimension extending longer than a width of the opening. The frame element may include at least one rib protruding from a peripheral wall defining the opening. The at least one affixation element is arranged secured against the peripheral wall. A thickness of the frame element at the opening is generally the same as a length of a stem extending from the base and carrying the head. The system may use any of the fastener members and variations of the frame element described herein.

A method for affixing a fastener member to a structure includes providing an attachment opening on the structure, attaching the fastener member to the structure. The fastener member includes a base having first and second sides, a plurality of fastening elements extending from a first side of the base, and an affixation element extending from the second side of the base. The method further includes affixing the affixation element to the structure about the attachment opening.

A thickness of the frame element at the opening is generally the same as a length of a stem extending from the base and carrying the head. The head may have a length greater than a width of the stem. The method may include using any of the fastener elements described herein and attaching the same to the attachment opening.

In another embodiment, the fastener member may be permanently secured to a structure. According to one variation, the fastener member is secured within a recess formed by a structure, and a fastener retains the fastener member within the recess. The recess can prevent rotation or shifting of the fastener member relative to the structure, whereas the fastener keeps the fastener member from pulling away from the structure.

The fastener member may be formed from a material different from the structure, either more rigid or more flexible. For example, the structure may be constructed from carbon fiber or aluminum, and may be more or less rigid than the fastener member. While it may not be feasible to construct the fastener member from certain types of structure, but it may be desirable to have a strong fastener member rather than conventional hook material in known hook and loop systems and this is achieved by providing an injected molded fastener member that can be selectively secured to a structure.

BRIEF DESCRIPTION OF THE DRAWINGS

These and other features, aspects, and advantages of the present disclosure will become better understood regarding the following description, appended claims, and accompanying drawings.

FIG. 10 is a perspective view showing a third embodiment of a fastener member.

FIG. 11 is a schematic sectional rear view showing affixation of the fastener member of FIG. 10 onto a frame element.

FIG. 12 is a schematic sectional front view showing affixation of the fastener member of FIG. 10 onto a frame element.

FIG. 13 is a cross-sectional view taken along line XIII-XIII in FIG. 12.

Figure 1:
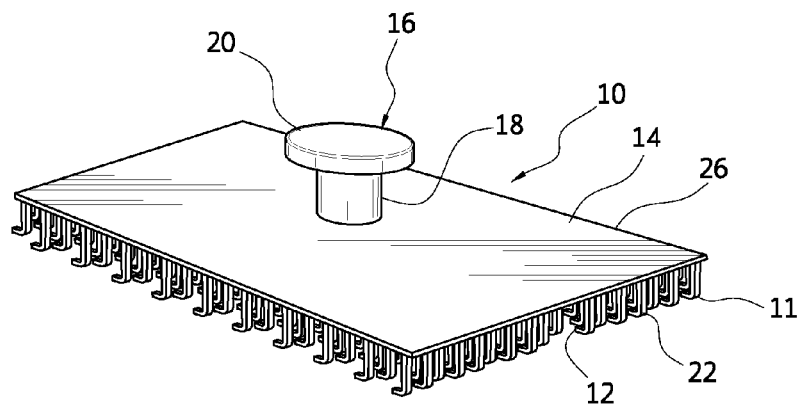
FIG. 1 is a perspective view showing a first embodiment of a fastener member.

The drawing figures are not necessarily drawn to scale, but instead are drawn to provide a better understanding of the components, and are not intended to be limiting in scope, but rather to provide exemplary illustrations. The figures illustrate exemplary embodiments of a frame element in an orthopedic device, and in no way limit the structures or configurations of a fastener member and structure for receiving the fastener member according to the present disclosure.

DETAILED DESCRIPTION OF VARIOUS EMBODIMENTS

Under a first embodiment according to the disclosure, FIG. 1 depicts a fastener member 10 having a base 11 carrying a plurality of fastener elements 22 along a front side 12. A backside 14 of the base 11 includes an affixation element 16 arranged for securing to a structure. The affixation element 16 has a stem 18 defining a first end extending perpendicularly from the base 11 and a head 20 on a second end of the stem 18.

According to an embodiment, the backside 14 has a substantially flat contour. The base 11 may be substantially rigid or may be flexible to accommodate a shape of a frame member.

While the stem 18 is preferably cylindrical in shape, the head 20 preferably is not round and extends in length greater than a width or diameter of the stem 18. The head may have a variety of different shapes. The head 20 is a non-round component extending from opposed sides of the stem 18. Alternatively, the head has a diameter greater than the diameter of the stem.

The fastener member may be made from various materials. The body may be made of polymeric materials, such as polyvinyl chloride, polypropylene, or other engineering plastics. The base, affixation element, and the fastener elements may be formed as a unitary structure, or alternatively the affixation or the fastener elements may be secured to the base. The fastener member may be trimmable so the base periphery can be modified according to particular usage or a location along the frame element.

The fastener member may be rendered or formed in a substantially flexible condition or may be rendered or formed into a rigid condition, depending on the intended application and desired durability of the fastener member.

Figure 4:
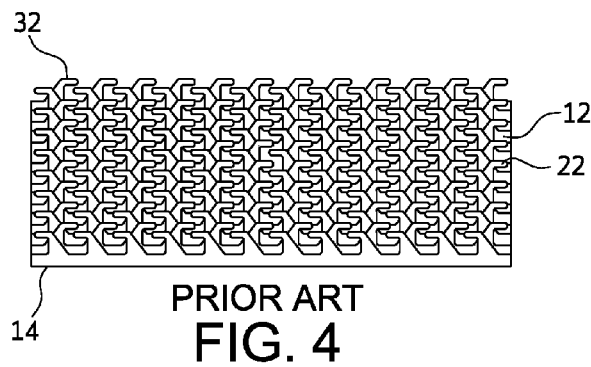
FIG. 4 is an exemplary perspective view of a prior art fastener element configuration.

The fastener elements may be arranged in the prior art example in FIG. 4. The fastener elements 22 are a plurality of hooks 32 arranged in alternating rows and integrally formed with the base 12 from the backside 14. The fastener element may be configured in a variety of ways, such as various shapes, materials, arrangements, numbers of elements; the hook elements may comprise structure capable of separable attaching to a loop material.

While the fastener member 10 is depicted as having a generally square or rectangular profile, the base periphery 26 may take on a variety of shapes and sizes. The base periphery is not limited to the shape and size depicted, and may be suitably adapted depending on the type of structure it is affixed to and to which the hook elements should engage. The fastener member is not limited to a single affixation element, but may include multiple affixation elements depending on the size and shape of the fastener element and the structure upon which it is affixed.

While affixation elements are described in combination with this embodiment, the fastener members described may be attached to a structure in a variety of ways. The affixation element may be removed or provided in combination with ultrasonic welding, riveting, insert molding, or an adhesive to assure that the fastener member is securely retained on the structure. The structure, such as the frame element, may include a recessed portion into which the fastener member is secured so that either the affixation element or the base other than the fastener elements protrude from a surface of the structure to minimize exposure of the fastener member and contribute to a streamlined configuration.

Figure 2:
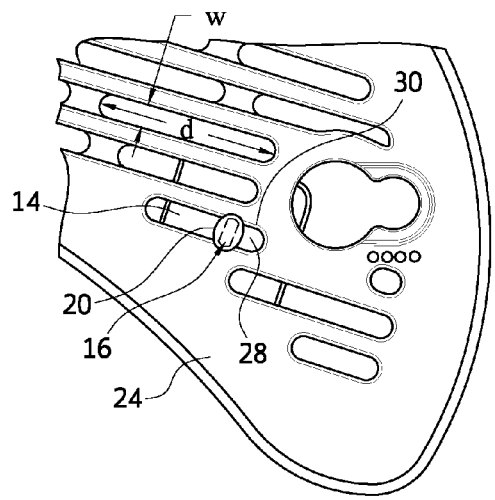
FIG. 2 is a schematic sectional rear view showing affixation of the fastener member of FIG. 1 onto a frame element.
Figure 3:
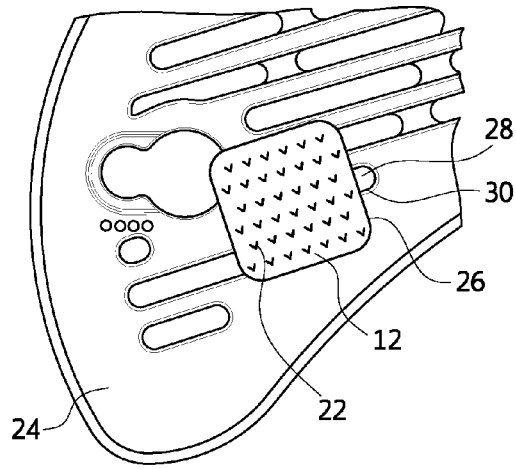
FIG. 3 is a schematic sectional front view showing affixation of the fastener member of FIG. 1 onto a frame element.

In reference to FIGS. 2 and 3, the fastener member 10 is shown as attached to a structure in a molded article or frame element 24 in an orthopedic device. An example of a frame element 24 is found in U.S. Pat. No. 7,198,610, granted on Apr. 3, 2007, and incorporated by reference. Examples of padding, spacer elements, straps and other components capable of securing to the fastener elements may also be found in U.S. Pat. No. 7,198,610.

The frame element 24 has a plurality of attachment openings 28 and corresponding peripheral walls 30 formed from the structure and delimiting the openings. In the example in FIGS. 2 and 3, the attachment openings take on the shape of elongate slots formed from the frame element. The width of the attachment openings is smaller than the length of the head of the fastener member and generally matches the diameter or width of the stem 18, although the length of the attachment openings may be significantly longer than the length of the head.

Figure 5:
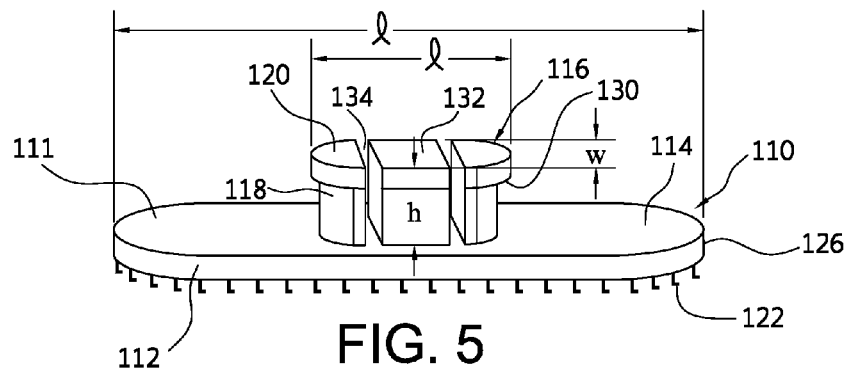
FIG. 5 is a perspective view showing a second embodiment of a fastener member.
Figure 8:
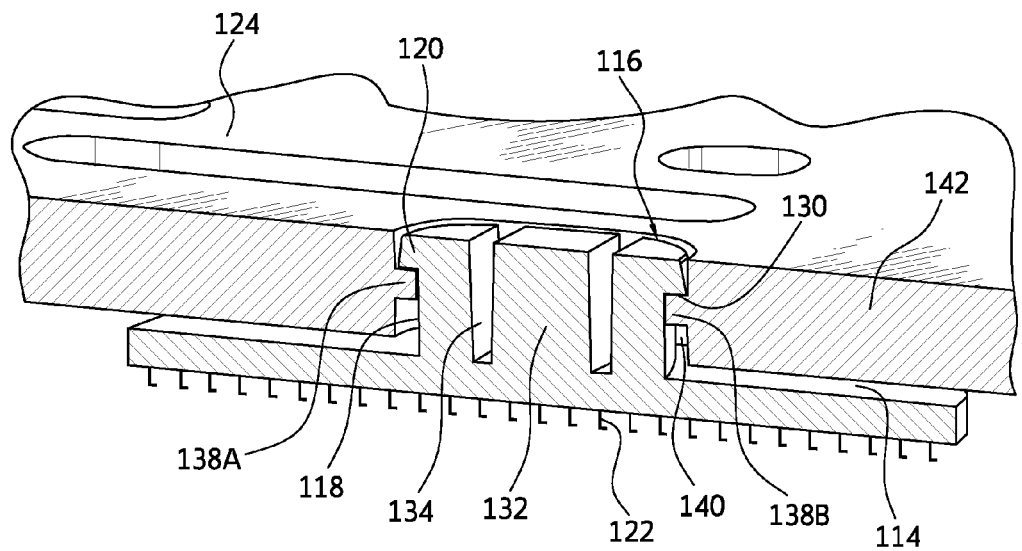
FIG. 8 is a cross-sectional view taken along line VIII-VIII in FIG. 7.

FIG. 2 shows how the width and length of the attachment openings is defined, whereas FIG. 5 shows how the width, length and height of the affixation element may be defined however the height of the stem in the fastener member 10 is defined between its first and second ends. FIG. 5 also shows how the length of the base can be defined. FIG. 8 shows how the thickness of the frame element may be defined.

As shown, the fastener member 10 is secured to the frame element 24 by securing the head 20 against a first surface 34 of the frame element beyond the peripheral walls 30 of the attachment openings 28. The backside 14 of the fastener member 10 is arranged adjacent to a second surface 36 of the frame element 24 due to the stem 18 having a height generally corresponding to the thickness of the walls 30 to assure that the backside 14 of the fastener member 10 is snugly secured against the second surface 36 of the frame element 24. The front side 12 of the fastener member 10 is arranged to readily expose the fastener elements 22.

When selecting where to install the fastener member 10, the clinician may choose among any of the openings adapted to receive the stem. The head is inserted through the opening such that the length of the head is generally parallel with the length of the opening. Once the correct position along the opening is selected, the clinician rotates the fastener member such that the length of the head is generally perpendicular to the length of the openings.

The fastener member may be adapted to slide relative to the walls of the opening, or alternatively snugly fit against the frame element without movement once placed into the desired location. Alternatively, the frame element may include recesses along either of the first or second frame surfaces at predetermined locations to receive the head once rotated in a secure placement.

In referring to the embodiment of FIG. 5, another fastener member 110 is provided having a variation of an affixation element 116. The fastener member 110 has a base 111 carrying a plurality of fastener elements 122 along a front side 112. A backside 114 of the base 111 includes an affixation element 116 arranged for securing to a structure.

The affixation element 116 has a pair of resiliently flexible side legs 118 spaced apart by gaps 134 on opposed sides of a center leg 132. The head 120 extends from both of the side legs 118 and generally take on a mirror image of each other. Each head 120 includes a flange 130 that protrudes from the stem 118. The periphery of the head 120 has sloped edges 121 outside of the portion adjacent the center leg 132.

Figures 6, 7:
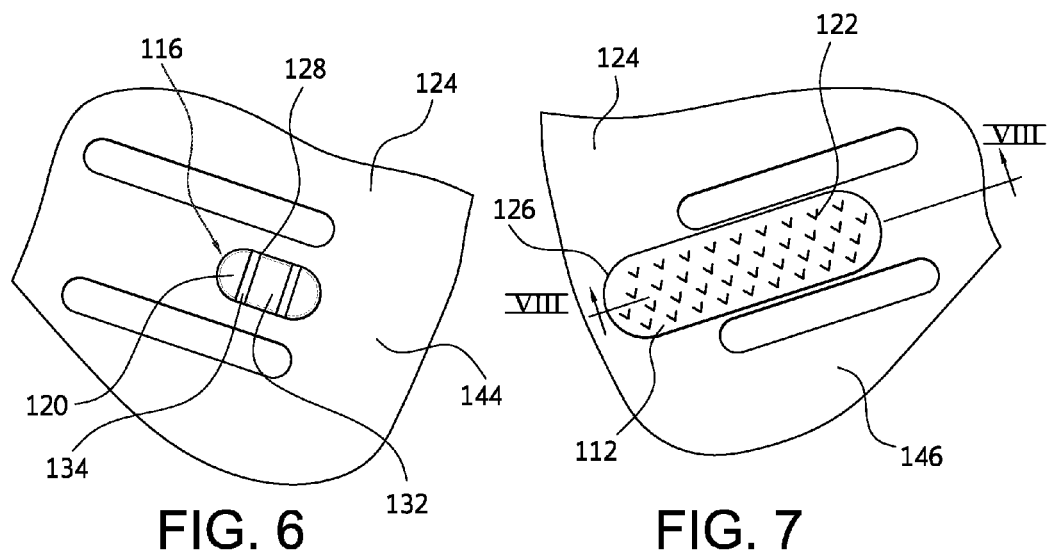
FIG. 6 is a schematic sectional rear view showing affixation of the fastener member of FIG. 5 onto a frame element.
FIG. 7 is a schematic sectional front view showing affixation of the fastener member of FIG. 5 onto a frame element.

As shown in FIGS. 5 and 7, the base periphery 126 is generally elongate and has rounded edges. According to this embodiment, the fastener member is adapted to provide greater surface in a length direction of the fastener member for exposing the fastener elements 122 from the front side 112.

When installed on the frame element 124, the fastener member 110 is secured to the frame element 124 by securing the flanges 130 of the heads 120 within an attachment opening 128 so as not to extend beyond a surface of the frame element. The head 120 of the affixation element 116 generally corresponds in shape to the periphery of the attachment opening 128. The backside 114 of the fastener member 110 is arranged adjacent to a second surface 146 of the frame element 124 due to the side legs 118 snugly securing against the frame element 124. The front side 112 of the fastener member 110 is arranged to readily expose the fastener elements 122.

Figure 9:
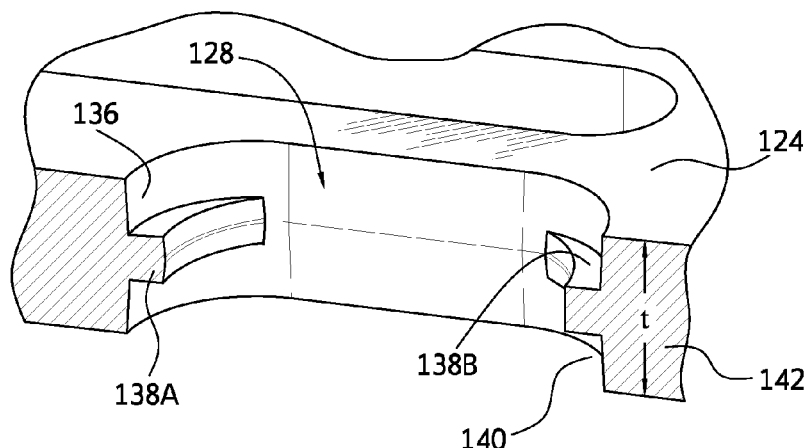
FIG. 9 is a schematic view of FIG. 8 without the fastener member.

As shown in FIG. 8, the height of the affixation element 116 corresponds to the thickness 142 of the frame element 124. As better depicted in FIG. 9, the frame element 124 defines ribs 138A, 138B defined between upper and lower wall portions defining the attachment opening 128. When the affixation element 116 is inserted into the attachment opening 128 with some degree of force, the sloped edges 121 of the head 120 slide against the ribs 138A, 138B and the side legs 118 resiliently bend toward the center leg 132. Once the flanges 130 pass past the ribs 138A, 138B, the flanges 130 return to their initial state such that the flanges 130 extend over the ribs 138A, 138B to lock or snap-fit the fastener member relative to the frame element 124. Further movement of the affixation element 116 is prevented since the height of the affixation element 116 generally corresponds to the thickness 142 of the frame element 124.

In referring to FIG. 10, another embodiment of a fastener member 210 has opposed affixation elements 216A, 216B protruding from a base 211 carrying a plurality of fastener elements 222 along a front side 212. Each of the affixation elements 216A, 216B defines a resilient flexible side leg 218 carrying a head 220 having a sloped face 221 and extending to a flange 230. The sloped faces 221 are arranged in opposed directions of the length of the base 211. As with the other fastener members, the base has a periphery 226 that is both adaptable in shape and size.

According the embodiment of FIG. 10 and depicted in FIGS. 11-13, the fastener member 210 is secured against the wall portions 236 of a pair of attachment openings 228A, 228B. The side legs 218 are arranged to flexibly extend into the attachment openings 228A, 228B along the wall portions 236 and snap-fit against the wall portions such that the flanges 230 extend over a surface of the frame element and the side legs 216 are resiliently urged against the wall portions 230.

Figure 14:
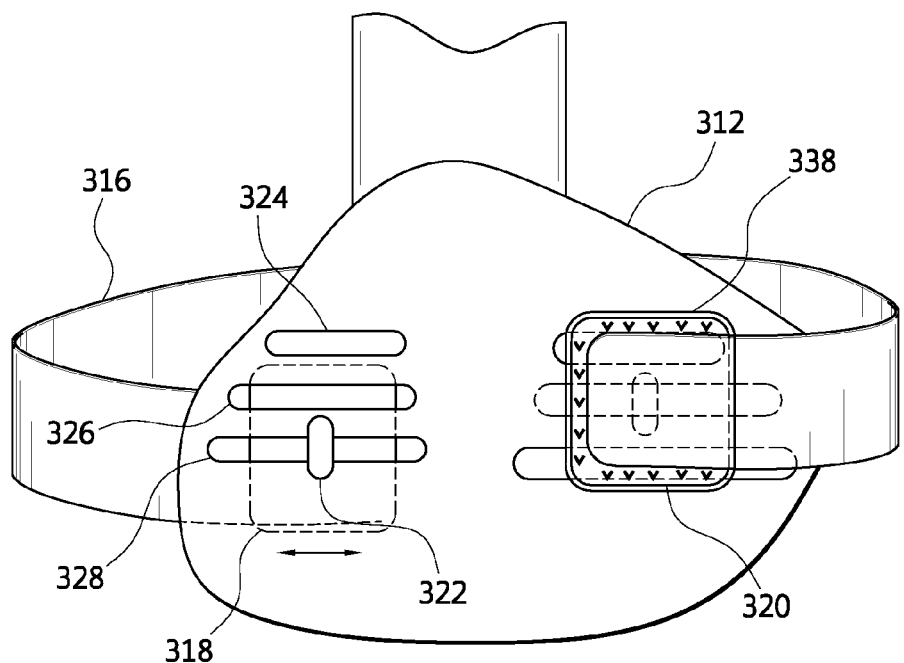
FIG. 14 is a schematic view showing a configuration of a set of fastener members securing a strap to a frame element.

As exemplified in FIG. 14, a set of fastener members 318, 320 may be arranged on a frame element 312 in a variety of configurations, and a strut 314 may be connected to other brace components. In this example, the frame element 312 defines a plurality of horizontally oriented attachment openings 324, 326, 328 on opposed sides, and received the fastener members 320, 322. A strap 316 has opposed end portions that engage the fastener members 318, 320.

The fastener members 320, 322 may be arranged under the embodiments described. As depicted in FIG. 14, the fastener members 318, 320 that generally correspond to the fastener member 10. At least h the fastener member 318 includes an affixation element 322 adapted to slide relative to the frame element, although delimited by ends of the attachment opening thereby permitting some adjustability while when a user wears the brace. A pad having some frictional component may be on the strap which prevents migration of the strap despite the ability of the fastener members to travel. Tension of the strap on the user may likewise limit movement of the fastener member. A clinician can select among one of the attachment openings 324, 326, 328 arranged according to height of the frame element 312.

FIG. 14 exemplifies how a recess 338 may be formed on a structure, as in the frame element 314, and corresponds in shape with the fastener member 320 to retain the fastener member 320 in place, and also to minimize or eliminate clearance of the base other than the fastener elements from a surface of the frame element. The fastener member 320 may be attached to the frame element 314 in any manner described.

As shown, the fastener members 318, 320 are placed on opposed surfaces of the frame element. The fastener members are not limited to this arrangement, and may be likewise placed along the same surface. Multiple fastener members may be attached along the same attachment opening to lengthen the area that includes fastener elements if it is found the given length of an individual fastener element is insufficient. The fastener members may be supplemented with an adhesive besides the mechanical coupling, and may also be in combination with adhesively applied hook material pieces in a retrofit condition.

Figure 15:
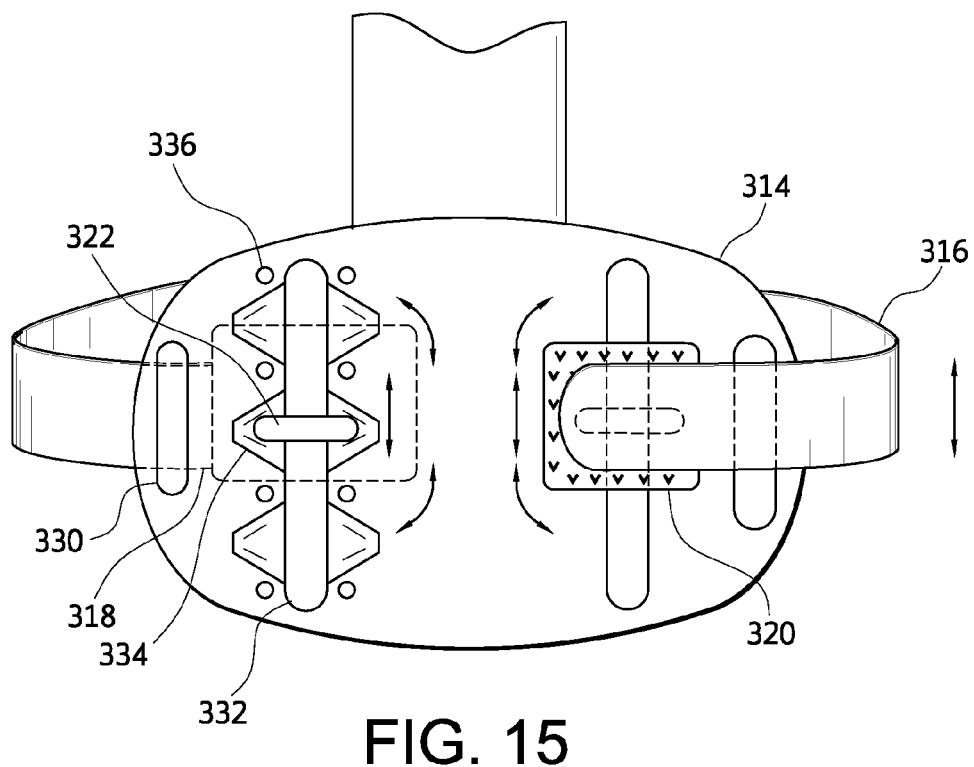
FIG. 15 is a schematic view showing the set of fastener members securing to a strap as in FIG. 14 on a variation of a frame element.

In referring to FIG. 15, an alternative frame element 314 defines a plurality of vertically oriented attachment openings 330, 332 arranged at opposed sides of the frame element 314. The frame element is not limited to the arrangement of vertically or horizontally oriented attachment openings on opposed sides of the frame element. Attachment openings can be in any orientation and at any location on the frame element to receive a fastener member.

The frame element 314 may include recesses 334 into which an affixation element 322 may be located. The recesses 334 may be arranged in a manner which permits the affixation element 322 and hence the corresponding fastener member 322 may rotate or linearly travel within a certain range. The frame element 314 may include stop protrusions 336 which likewise limit travel of the fastener member by stopping rotational and linear movement of the fastener member.

The frame element 314 allows for the strap 316 to adjust in height, and rotate according to movement of the user. In a knee brace, the strap may be allowed to slide upwards and downwards while the leg moves between extension and flexion, especially if the brace includes some frictional contact with the user such as a friction component on a liner. The motion of the fastener members may reduce shear forces exerted on the skin of the user.

Despite the embodiments described, attachment of the fastener member on a frame element may be arranged so the fastener member is fixed in place, or is movable as discussed above with the embodiments of FIGS. 14 and 15.

Figure 16:
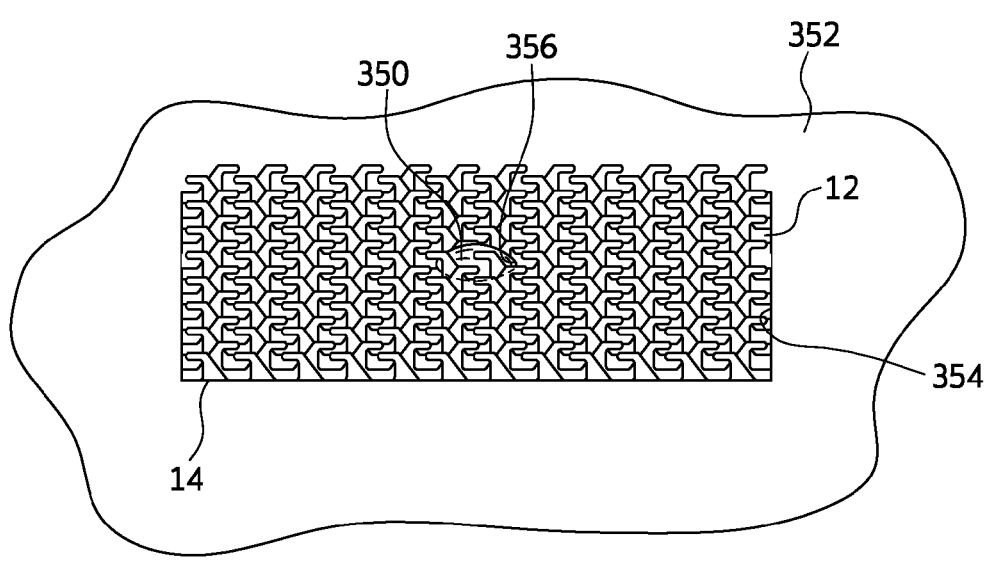
FIG. 16 is a schematic view showing a fastener member secured to a frame element.

In another embodiment exemplified by FIG. 16, the fastener member 12 may be permanently secured to a structure 352. According to one variation, the fastener member 12 is secured within a recess 354 formed by the structure 352, and a fastener 350, such as a rivet, retains the fastener member within the recess 354. An opening 356 may be provided within the structure to accommodate the fastener 350. The fastener member 12 may be sized and configured to snugly fit within the recess 354. The recess 354 can prevent rotation or shifting of the fastener member 12 relative to the structure 352, whereas the fastener 350 keeps the fastener member 12 from pulling away from the structure 352. Alternatively, the fastener member 12 may be secured to the structure 352 by an adhesive.

The fastener member may be formed from a material different from the structure, either more rigid, more flexible or the same. For example, the structure may be constructed from carbon fiber or aluminum and is essentially more rigid than the fastener member. It may not be feasible to construct the fastener member from the structure, but it may be desirable to have a strong fastener member rather than conventional hook material in known hook and loop systems where the hooks are constructed from nylon or similar material substantially dissimilar from the structure.

The fastener members may be configured to retrofit existing frame elements in existing orthopedic devices having frame elements defining suitable openings capable of interengaging various means for affixing the fastener members to the frame element. The frame element can receive another type of orthopedic device feature, for example liners, padding, and straps, carrying suitable loop element or other material or structure capable of securely engaging with fastener elements on the fastener member.

While the structure is described with an orthopedic device, the structure may comprise any form of structure for any type of device requiring a fastener member under the embodiments described.

The skilled artisan will recognize the interchangeability of various features from different embodiments. Besides the variations described, other known equivalents for each feature can be mixed and matched by one of ordinary skill in this art to construct fastener members and structural element for attachment of the fastener members under principles of the present disclosure.

Although the embodiments have been disclosed in certain exemplary embodiments and examples, it therefore will be understood by those skilled in the art that the present invention extends beyond the disclosed embodiments to other alternative embodiments and/or uses of the invention and obvious modifications and equivalents. It is intended that the scope of the present invention disclosed should not be limited by the disclosed embodiments described above.

The invention claimed is:

1. An orthopedic device comprising a frame element, a brace component, and a fastener member for mechanical affixation of the brace component to the frame element, the fastener member including:
   a base having first and second sides;
   a plurality of hook fastening elements extending from a first side of the base;
   an affixation element extending from the second side of the base and arranged to mechanically affix to at least one of a plurality of attachment openings of the frame element;
   wherein the affixation element has a head defining a length dimension extending longer than a width of at least one of a plurality of attachment openings;
   wherein each of the at least one of a plurality of attachment openings is formed as an elongate slot such the fastener member slides relative to walls surrounding the elongate slot along a length of the elongate slot;
   wherein the fastener member is secured to the frame element into a secured configuration by rotating the fastener member so that a head of the fastener member is pressed against a first surface of the frame element beyond peripheral walls of the at least one of a plurality of attachment openings, an entirety of a backside of the base of the fastener member is arranged directly adjacent to a second surface of the frame element due to a stem carrying the head of the affixation element, which passes through the attachment opening, having a height corresponding to and the same as a thickness of the peripheral walls to assure that the backside of the fastener member is snugly secured without movement directly against the second surface of the frame element, wherein the head extends in length greater than a width or diameter of the stem and wherein the width of the at least one of a plurality of attachment openings matches the diameter or width of the stem of the fastener member, the fastener member being readjustable relative to the frame element from the secured configuration by rotating the fastener member so the length dimension of the head is parallel to the length of the at least one of a plurality of attachment openings;
   wherein the brace component is arranged to connect to the frame element and includes loop material for interengaging the plurality of hook fastening elements of the fastener member at a plurality of locations on the frame element corresponding to the plurality of attachment openings, and the brace component is selected from the group consisting of a strap and padding.

2. The orthopedic device of claim 1, wherein the frame element includes at least one recess about a peripheral wall defining the at least one of a plurality of attachment openings, the affixation element arranged to be secured against the peripheral wall.

3. The orthopedic device of claim 2, wherein the recess corresponds in shape to the fastener member to retain the fastener member in place.

4. The orthopedic device of claim 2, wherein the recess is arranged in size to eliminate clearance of the head from the second surface of the frame element.

5. The orthopedic device of claim 1, wherein the fastener member is formed in a substantially flexible condition.

6. The orthopedic device of claim 1, wherein the length of the at least one of a plurality of attachment openings is substantially longer than the length dimension of the head.

7. The orthopedic device of claim 1, wherein the head of the affixation element is arranged for being inserted through the at least one of a plurality of attachment openings such that the length dimension of the head is generally oriented parallel with the length of the at least one of a plurality of attachment openings, and rotated such that the length of the head is generally perpendicular to the length of the at least one of a plurality of attachment openings.

8. The orthopedic device of claim 1, wherein the frame element includes a recessed portion into which the base extends and which the fastening elements protrude outwardly from the frame element.

9. The orthopedic device of claim 1, wherein the base is flexible and arranged to accommodate a shape of the structure upon which the fastener member is affixed.

10. The orthopedic device of claim 1, wherein the frame element is rigid or semi-rigid.

11. The orthopedic device of claim 1, wherein the fastener member defines a base periphery substantially smaller than a base periphery defined by the frame element.

12. The orthopedic device of claim 11, wherein the base periphery of the fastener member fits within a base periphery defined by the frame element.

13. The orthopedic device of claim 1, wherein the base, affixation element and hook fastening elements are formed as a unitary structure from polymeric materials.

14. The orthopedic device of claim 1, wherein the base is trimmable so a base periphery is modifiable in shape and size.

15. The orthopedic device of claim 1, wherein the stem is cylindrical in shape along an entirety of its height.

16. The orthopedic device of claim 1, wherein the head includes a flange protruding from the stem and arranged parallel to the first surface of the frame element when the fastener member is snugly secured to the frame element.

17. In an orthopedic device, a method for securing a fastener member to a frame element having a plurality of openings by mechanical affixation to connect a brace component to the frame element, the fastener member including a base having first and second sides, a plurality of hook fastening elements extending from a first side of the base, an affixation element extending from the second side of the base and arranged to mechanically affix to an attachment opening of the frame element, the affixation element having a head defining a length dimension extending longer than a width of the plurality of attachment openings, the method comprising the steps of:
   selecting one of the plurality of attachment openings defined by the frame element for affixation of the fastener member;
   inserting the head into one of the plurality of attachment openings such that a length dimension of the head is aligned with a length of the one of the attachment openings;
   sliding the fastener member relative to the one of the plurality of attachment openings and selecting a location along the one of the plurality of attachment openings for affixing the fastener member;
   rotating the fastener member so the length dimension of the head is generally perpendicular to a length of the one of the plurality of attachment openings so the head snugly engages directly against a first surface of the frame element and an entirety of a first side of the base snugly is against a second surface of the frame element without movement at the location;

wherein the fastener member includes a stem carrying the head of the affixation element, which passes through the attachment opening, having a height corresponding to and the same as a thickness of peripheral walls of the frame element about the one of the plurality of attachment openings, wherein the head extends in length greater than a width or diameter of the stem and wherein the width of the at least one of a plurality of attachment openings matches the diameter or width of the stem of the fastener member;

applying the brace component to the fastener member such that loop material of the brace component engages the hook fastening elements, wherein the brace component is selected from the group consisting of a strap and padding.

18. The method of claim 17, further comprising the step of removing the fastener member after being secured to the frame element by rotating the length dimension of the head so it is parallel to the length of the one of the plurality of attachment openings.

\* \* \* \* \*